(12) United States Patent
Wallace et al.

(10) Patent No.: US 8,038,720 B2
(45) Date of Patent: Oct. 18, 2011

(54) METHODS AND DEVICES FOR INTRAGASTROINTESTINAL PROSTHESES

(76) Inventors: Jeffrey M. Wallace, Charlestown, RI (US); Peter J. Lukin, Norfolk, MA (US); Donald Coelho, Jr., Bellingham, MA (US); Gregory Amante, Holliston, MA (US)

( * ) Notice: Subject to any disclaimer, the term of this patent is extended or adjusted under 35 U.S.C. 154(b) by 343 days.

(21) Appl. No.: 11/269,394

(22) Filed: Nov. 8, 2005

(65) Prior Publication Data
US 2008/0221702 A1    Sep. 11, 2008

Related U.S. Application Data

(60) Provisional application No. 60/727,802, filed on Oct. 18, 2005.

(51) Int. Cl.
*A61F 2/04* (2006.01)
*A61M 5/00* (2006.01)
(52) U.S. Cl. ............... 623/23.65; 623/23.68; 604/8
(58) Field of Classification Search ........... 623/23.64, 623/23.65, 23.67, 23.7, 1.24, 1.26, 2.14, 623/2.18; 604/8, 909
See application file for complete search history.

(56) References Cited

U.S. PATENT DOCUMENTS

| | | | | |
|---|---|---|---|---|
| 213,186 | A | * | 3/1879 | Gassett ............... 137/512.1 |
| 3,402,710 | A | * | 9/1968 | Paleschuck .............. 128/887 |
| 5,306,300 | A | * | 4/1994 | Berry ................... 623/23.64 |
| 6,254,642 | B1 | * | 7/2001 | Taylor .................. 623/23.64 |
| 6,936,057 | B1 | * | 8/2005 | Nobles ..................... 606/194 |
| 7,146,984 | B2 | | 12/2006 | Stack et al. |
| 7,513,914 | B2 | | 4/2009 | Schurr |
| 7,666,180 | B2 | | 2/2010 | Holsten et al. |
| 7,678,068 | B2 | | 3/2010 | Levine et al. |
| 7,682,330 | B2 | | 3/2010 | Meade et al. |
| 7,695,446 | B2 | | 4/2010 | Levine et al. |
| 7,753,870 | B2 | | 7/2010 | Demarais et al. |
| 7,758,535 | B2 | | 7/2010 | Levine et al. |
| 7,766,861 | B2 | | 8/2010 | Levine et al. |
| 7,771,382 | B2 | | 8/2010 | Levine et al. |
| 7,789,848 | B2 | | 9/2010 | Gannoe et al. |
| 7,794,447 | B2 | | 9/2010 | Dann et al. |
| 7,833,280 | B2 | | 11/2010 | Stack et al. |
| 7,837,645 | B2 | | 11/2010 | Bessler et al. |
| 7,837,669 | B2 | | 11/2010 | Dann et al. |
| 7,846,138 | B2 | | 12/2010 | Dann et al. |
| 2003/0093117 | A1 | * | 5/2003 | Saadat ................... 606/221 |
| 2003/0216679 | A1 | * | 11/2003 | Wolf et al. ............... 604/8 |
| 2004/0122526 | A1 | * | 6/2004 | Imran ................. 623/23.65 |
| 2004/0148034 | A1 | * | 7/2004 | Kagan et al. ........... 623/23.65 |
| 2004/0172142 | A1 | * | 9/2004 | Stack et al. ............ 623/23.65 |
| 2004/0254636 | A1 | * | 12/2004 | Flagle et al. .......... 623/1.24 |
| 2005/0197714 | A1 | * | 9/2005 | Sayet .................. 623/23.65 |
| 2005/0228504 | A1 | * | 10/2005 | Demarais ............. 623/23.65 |
| 2005/0273060 | A1 | * | 12/2005 | Levy et al. ............ 604/192 |
| 2005/0288694 | A1 | * | 12/2005 | Solomon ................ 606/157 |

(Continued)

FOREIGN PATENT DOCUMENTS

EP    2 191 795 A1    6/2010

*Primary Examiner* — Alvin J. Stewart
(74) *Attorney, Agent, or Firm* — Wolf, Greenfield & Sacks, P.C.

(57) ABSTRACT

An intragastric and/or intragastrointestinal device may include a prosthesis, which may reside within the gastrointestinal tract lumen. The device may include a restrictive element that constricts or restricts the gastrointestinal tract lumen, limiting the amount of food and/or fluid an individual consumes.

22 Claims, 4 Drawing Sheets

U.S. PATENT DOCUMENTS

| | | |
|---|---|---|
| 2006/0020327 A1* | 1/2006 | Lashinski et al. ............ 623/1.25 |
| 2007/0021651 A1* | 1/2007 | Gobel ............................ 600/31 |
| 2007/0255394 A1* | 11/2007 | Ryan ............................ 623/1.24 |
| 2009/0093767 A1 | 4/2009 | Kelleher |
| 2009/0093837 A1 | 4/2009 | Dillon |
| 2009/0093839 A1 | 4/2009 | Kelleher |
| 2009/0138093 A1* | 5/2009 | Bell et al. ................... 623/23.64 |
| 2010/0069819 A1 | 3/2010 | Laufer et al. |
| 2010/0145472 A1 | 6/2010 | Holsten et al. |
| 2010/0298631 A1 | 11/2010 | Stack et al. |
| 2010/0298632 A1 | 11/2010 | Levine et al. |

* cited by examiner (A)

(B)

METHODS AND DEVICES FOR INTRAGASTROINTESTINAL PROSTHESES

This application claims priority to U.S. Provisional Patent Application Ser. No. 60/727,802, filed Oct. 18, 2005, which is hereby incorporated by reference in its entirety.

FIELD OF INVENTION

This present invention relates to methods and devices for intragastrointestinal prostheses

BACKGROUND

Obesity, as defined by a body mass index (BMI) of 30 kg/m² or more, is a rapidly growing problem, currently affecting more than 30% of adults in the United States. Morbid obesity, as defined by a body mass index of 40 kg/m² or more or a BMI of 35 kg/m² or more in the presence of co-morbidities is also prevalent, affecting 3.1% of men and 6.7% of women. Obesity is commonly associated with many serious medical disorders including heart disease, diabetes, hypertension, hyperlipidemia, hypercholesterolemia, osteoarthritis and sleep apnea. In addition, approximately 300,000 adults in the U.S. die each year due to obesity-related causes.

The primary treatment objective for obese patients is weight reduction, which can improve co-morbid conditions and also reduces risk factors for disease. Even moderate weight loss (5%-10% of initial weight) produces health benefits and has been associated with marked reductions in the risk for the medical disorders listed above. While non-operative and pharmacologic weight loss therapies have met with only limited success, surgical intervention pharmacologic weight loss therapies have met with only limited success, surgical intervention for morbid obesity, most frequently gastric bypass, is becoming increasingly common. However, the decision to undergo gastric bypass is a difficult one. Patients who choose to undergo gastric bypass are making a serious commitment to permanent life-style changes and are at risk for developing metabolic/nutritional complications resulting from the long-term malabsorptive effects of gastric bypass and food intake restriction. Long-term complications of gastric bypass including anemia secondary to iron or $B_{12}$ deficiency, mineral deficiencies (hypokalemia and hypomagnesia) and bone disease associated with secondary hyperparathyroidism are not uncommon. These conditions can be serious thereby necessitating lifelong medical follow-up to monitor for such events.

Although various procedures exist for the surgical treatment of morbid obesity, the Roux-en-Y gastric bypass (RYGB) has been identified as the gold standard for morbidly obese patients when non-invasive interventions have failed. The RYGB procedure entails the creation of a small gastric pouch to which the distal jejunum is attached via creation of an anastomosis referred to as a gastrojejunostomy (GJ). The procedure excludes more than 95% of the stomach, all of the duodenum and the proximal jejunum from digestive continuity. Weight loss is thought to result from reduced intake volume due to the small gastric pouch and limited GJ diameter, as well as from malabsorption due to the bypass of the proximal jejunum. The procedure is associated with a mean of 65-75% excess weight loss with 1% mortality and 10% morbidity.

Despite the favorable safety and effectiveness profile of the RYGB procedure, technical complications and inadequate weight loss may occur. Serious complications are not uncommon after open bariatric procedures. Adhesion formation may contribute to small bowel obstructions, which may require an additional operation for the patient. Incisional hernias are another complication associated with abdominal surgical procedures and have been shown to occur at a much higher rate after open gastric bypass surgery than after laparoscopic bypass surgery.

The significant morbidity associated with traditional weight loss surgery emphasizes the importance of the development of minimally invasive interventions that will result in patient weight loss, which may improve co-morbid conditions and also reduce risk factors for disease. Additionally, a minimally invasive or intragastrointestinal approach will minimize or eliminate many of the risks associated with open and laparoscopic procedures.

BRIEF DESCRIPTION OF THE DRAWINGS

Certain embodiments of the invention are described with reference to the accompanying drawings, which, for illustrative purposes, are not necessarily drawn to scale.

DETAILED DESCRIPTION

Figure 1:
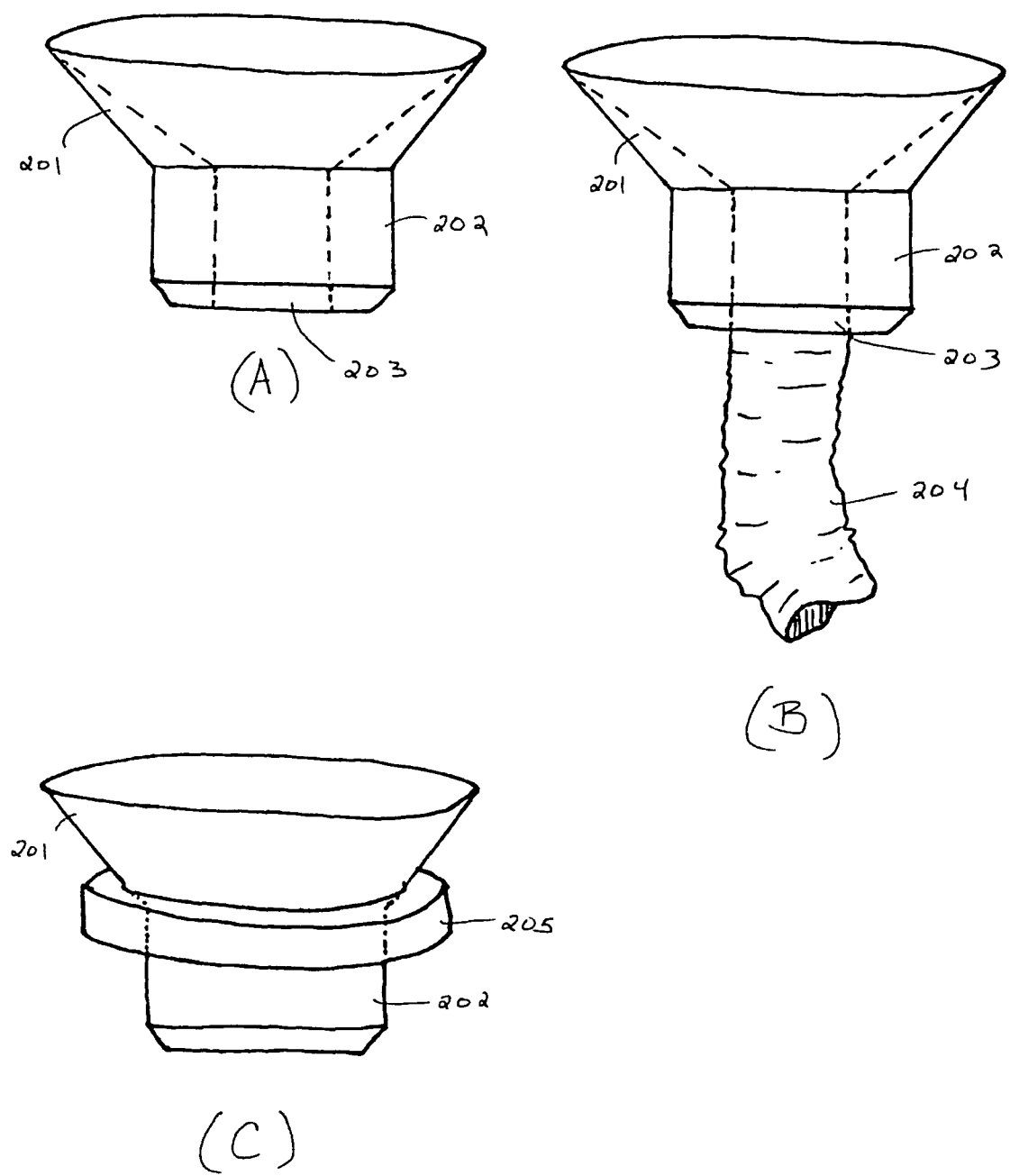
FIGS. 1A, 1B and 1C illustrate an embodiment of an intragastrointestinal device or prosthesis with a flanged portion that may assist in fixation. An optional distal portion is also shown.

Presented here are several embodiments of the invention that may pertain to an intragastric and/or intragastrointestinal device including, but not limited to, an intragastrointestinal prosthesis. Certain embodiments may include devices and/or prostheses that may reside within, but not limited to, the gastrointestinal tract lumen. The gastrointestinal tract may include, but is not limited to, the stomach, esophagus, intestines, colon, rectum, anus, and other areas continuous with the lumen of the gastrointestinal tract. Certain embodiments of the present invention may include devices and/or prostheses that may reside outside the gastrointestinal tract lumen or devices and/or prostheses that may reside at least partially within the gastrointestinal tract lumen. Certain embodiments may incorporate a means to limit the amount of food and/or fluid an individual intakes (which may be defined as a restrictive device element) through methods including, but not limited to, constricting or restricting the gastrointestinal tract lumen volume. Such embodiments may cause a feeling of fullness or satiety more rapidly, causing the individual with the embodied device incorporating the restrictive device element to potentially stop eating and therefore decrease food and/or fluid intake. Certain embodiments include a restrictive device element, wherein the restrictive device element may be implemented as a stoma or lumen within or incorporated into an intragastrointestinal device or prosthesis. Such an intragastrointestinal device or prosthesis may be deployed in the stomach and/or gastrointestinal tract lumen, such that the intragastrointestinal device or prosthesis may regulate or affect the flow of swallowed food and/or fluid through the stomach and/or gastrointestinal tract lumen.

Certain embodiments may incorporate a means to limit the absorption of at least portions of swallowed food and/or fluid into an individual's body and/or circulatory system (which may be defined as a malabsorptive device element). Such embodiments may include a non-absorptive or partially-absorptive channel, which at least a portion of the swallowed food and/or fluid may pass through. Such a channel may block or partially block the ability of the gastrointestinal tract from absorbing or uptaking portions of the swallowed food into the body or circulatory system.

In preferred embodiments, an intragastrointestinal device or prosthesis may be placed within the lumen of the stomach. Embodiments may be placed in the stomach such that the intragastrointestinal device or prosthesis may divide or partition the stomach lumen's space. The stomach lumen's space may, be divided into a proximal portion, which may include, but is not limited to, the portion of the stomach lumen between the intragastrointestinal device or prosthesis and the gastroesophageal junction (which may be referred to as the proximal portion of the stomach) and a distal portion, which may included, but is not limited to, the portion of the stomach lumen between the intragastrointestinal device or prosthesis and the pylorus (which may be referred to as the distal portion of the stomach). It should be noted that the aforementioned partitioning embodiment represents one or many possible partitioning embodiments. It should also be noted that the intragastrointestinal device or prosthesis may partition the gastrointestinal tract lumen in an analogous way. In preferred embodiments of the present invention, the volume of the proximal portion of the stomach may be selected from within the range of about 10-30 ml.

In certain embodiments of the present invention, the intragastrointestinal device or prosthesis may partition a portion of the gastrointestinal tract lmen. In one example, the device may partition the gastrointestinal tract into a proximal portion and a distal portion (with the luminal space of the proximal portion being closer to the oral cavity and the distal portion being closer to the anus. The intragastrointestinal device or prosthesis may regulate or affect the flow of swallowed food and/or fluid as it may pass from the proximal portion of the gastrointestinal tract to the distal portion of the gastrointestinal tract. In such embodiments, the intragastrointestinal device or prosthesis may incorporate a restrictive device element, which may be implemented as one or more of elements that may regulate or affect the flow of swallowed food and/or fluid.

In certain embodiments of the present invention, the embodied device or prosthesis may preferably be placed at narrowings or bottlenecks of the gastrointestinal tract lumen. Such narrowings, bottlenecks, or points of stricture within said lumen (which may be referred to as a stricture point or stricture points) may provide a seat or preferable position for the intragastrointestinal device or prosthesis to reside or at least partially reside within the gastrointestinal lumen. Certain embodiments of a stricture point may include, but are not limited to, naturally occurring stricture points, such as, but not limited to, the gastroesophageal junction, the pylorus, the anal sphincter, or any other naturally occurring or partially naturally occurring narrowing of the gastrointestinal lumen. Alternatively, embodiments of a stricture point may include, but are not limited to, altered anatomy stricture points, such as, but not limited to, at least a portion of a band of material that may be wrapped around at least a portion of the gastrointestinal tract that may constrict or restrict the lumen of said portion of the gastrointestinal tract, an anastomoses that may be between two or more lumens, an anastomoses that may be between two or more portions of the same lumen, a surgical opening into a lumen that may enter in from the same or a different lumen, or a constriction or restriction of the gastrointestinal lumen that may be caused by at least a portion of a pathology.

A preferred embodiment of a stricture point within the stomach may include, but is not limited to, a band of material wrapped around at least a portion of the stomach wherein a portion of the stomach's lumen is constricted or restricted. Other preferable embodiments of a stricture point may include, but is not limited to, an anastomosis between at least a portion of the lumen of the stomach and at least a portion of the lumen of the intestines, and a surgical opening from the stomach's lumen into the abdominal cavity.

FIG. 1 illustrates potential embodiment of an intragastrointestinal device or prosthesis. Such an embodiment may be seated at a stricture point or narrowing where the lumen of the embodiment (203) may act as a restrictive device element. The illustrated embodiment incorporates a flanged portion (201) which may have a greater dimension than the body portion (202). As illustrated in FIG. 1A, the embodied intragastrointestinal device or prosthesis may incorporate a restrictive device element, embodied by the device's lumen (203) Optionally, as illustrated in FIG. 1B, the embodied device may include a distal portion (204). Such a distal portion (204) may be at least partially continuous with the body portion's lumen (203). Such a distal portion (204) may incorporate a malabsorptive device element. In the preferred embodiment, the greatest dimension of the flanged portion (201) may be larger than a inner dimension of the stricture point or narrowing. This embodied aspect is illustrated in FIG. 1C. In said embodiments, the body portion (202) has a dimension which may be less than an inner dimension of a stricture point or narrowing (illustrated in FIG. 1C as element 205). Additionally in the embodiment illustrated in FIG. 1C, the flanged portion (201) may have a dimension which may be greater than a inner dimension of a stricture point or narrowing (205). In these or similar embodiments, the body portion may move through the stricture point or narrowing from the proximal portion of the stomach and/or gastrointestinal tract to the distal portion (or understandably from the distal portion to the proximal portion of the stomach and/or gastrointestinal tract). However, the dimension of the flanged portion (201) may be larger than the inner dimension of the stricture point or narrowing (205), and as a result, the embodied intragastrointestinal device or prosthesis may not be able to pass through the stricture point or narrowing. In such embodiments, the device may be fixated or seated on the stricture point or narrowing, allowing the intragastrointestinal device or prosthesis to remain in place.

Many embodiments of the present invention are possible. In certain embodiments, the intragastrointestinal device or prosthesis may comprise at least two flanged portions. In preferred embodiments, one such flanged portion may reside at least partially within the proximal portion of the gastrointestinal tract lumen. In preferred embodiments, one such flanged portion may reside at least partially within the distal portion of the gastrointestinal tract lumen. When the embodied intragastrointestinal device is preferably deployed and/or seated at a stricture point, the flanged portion that may reside within at least a portion of the proximal portion of the gastrointestinal tract lumen may cause an opposing force to said device or prosthesis from potentially moving in the direction of the proximal portion to distal portion of the gastrointestinal tract lumen. In certain embodiments, when the intragastrointestinal tract device or prosthesis is preferably deployed and/or seated at a stricture point, the flanged portion that may reside within at least a portion of the distal portion of the gastrointestinal tract lumen may cause an opposing force to said device or prosthesis from potentially moving in the direction of the distal portion to the proximal portion of the intragastrointestinal tract lumen.

In certain embodiments, one or more flanged portions of the intragastrointestinal device or prosthesis may be embodied in one of more states. It may be possible in certain embodiments that one or more flanged portions may alternate between one or more states, including a state wherein the greatest dimension of one or more flanged portions may be less than the inner or internal dimension of a stricture point (which may allow the intragastrointestinal device to be more easily deployed and/or placed at a stricture point), and a state wherein the greatest dimension of one or more flanged portions may be greater than the internal dimension of a stricture point (which may allow the intragastrointestinal device to be fixated or seated at the stricture point). In preferred embodiments, the intragastrointestinal device my alternate between states of the flanged portion. The alteration between states of an embodied intragastrointestinal device or prosthesis may allow for easier deployment at a stricture point, while the embodiment may still provide fixation to at least partially remain in place at said stricture point. Multiple embodiments of the present invention are possible.

Figure 2:
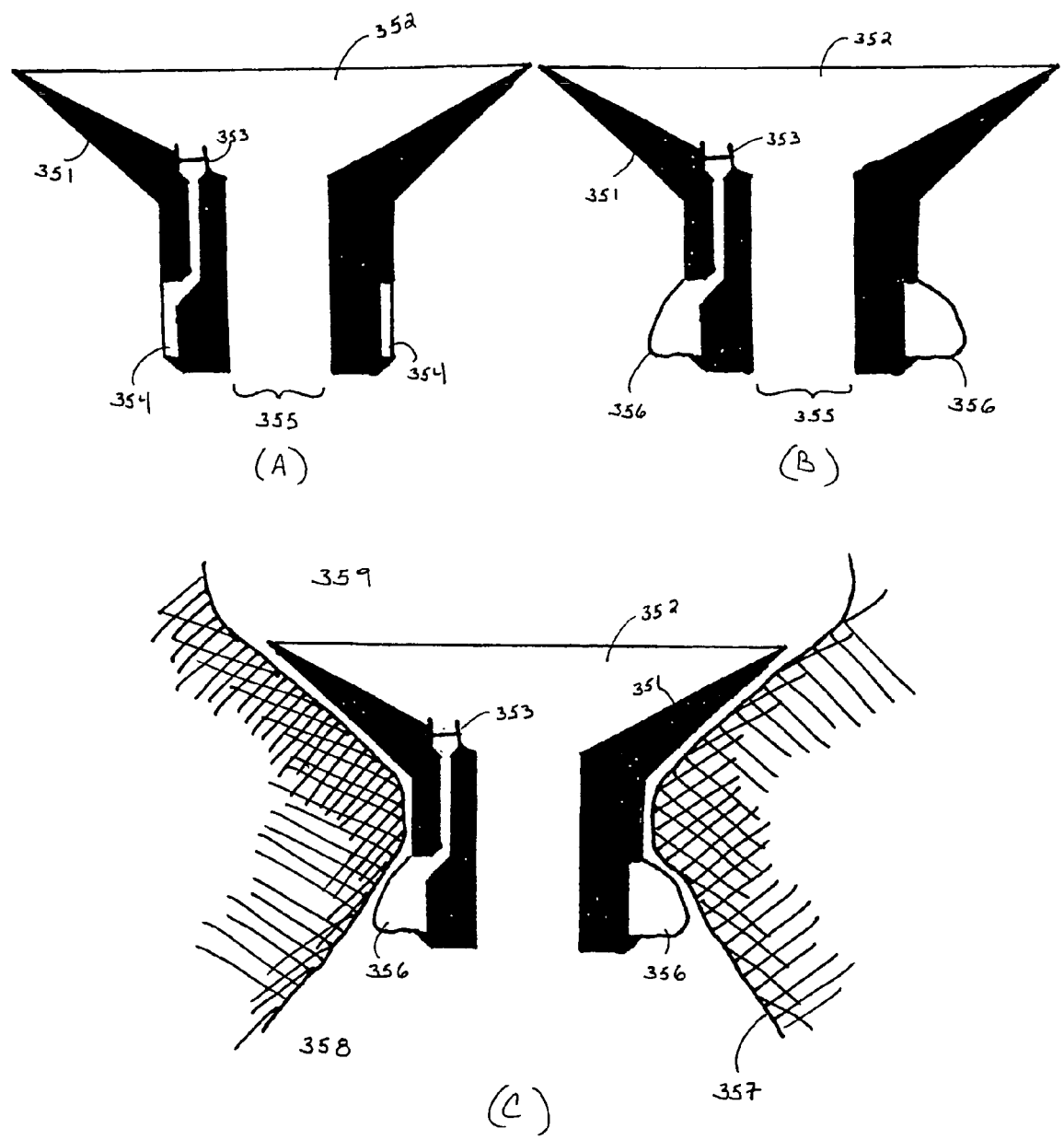
FIGS. 2A, 2B and 2C illustrate an embodiment of an intragastrointestinal device or prosthesis with adjustable portion that may aid in fixation.

FIG. 2 illustrates a cross-sectional view of an embodiment of the invention. In a manner akin to the embodiments shown in FIG. 1, the embodiment in FIG. 2 may include a flanged portion (351 & 352) that may reside in the proximal portion of the gastro-intestinal tract lumen. Food and/or fluid that are swallowed may enter through the embodied device from the opening in the flanged portion (352) and may enter into the lumen (355) of the embodied device. The embodied intragastrointestinal device or prosthesis may incorporate a restrictive device element. Optionally, but not shown in FIG. 2, the embodied device or prosthesis may contain a distal portion (similar as but not limited to a means embodied by the distal portion 204 shown in FIG. 1B) that may act as a malabsorptive device element.

The embodiment illustrated in FIG. 2 may also contain an expandable reservoir (354 & 356) that may reside as part of the body portion of the embodied intragastrointestinal device or prosthesis. Said reservoir may be filled with, but not limited to, saline, fluid, or gas. The embodied intragastrointestinal device or prosthesis may also incorporate a reservoir port (353) that may be positioned on the embodiment (illustrated in FIG. 2, but not limited to residing on the flanged portion 351). One embodiment of the port system that may be implemented on the embodied device or prosthesis may include a membrane which can be accessed by a needle or syringe. The embodiment may be designed such that the needle or syringe may increase or decrease the amount of medium within the reservoir. Said needle or syringe may be, but is not limited to, percutaneously or endoscopically delivered.

The reservoir port (353) in the embodiment shown in FIG. 2 may allow the embodied device or prosthesis to expand or contract the expandable reservoir (354 & 356). By doing this, the embodied device or prosthesis may add a fixation element that may keep the embodied device or prosthesis from disengaging or moving away from the stricture point or narrowing. In the contracted state, shown in FIG. 2A, the expandable reservoir (354) may have been reduced such that the inner dimension of the body portion plus the expandable reservoir (354) may be less than the inner dimension of the stricture point or narrowing. In the expanded state, shown in FIG. 2B, the expandable reservoir (356) has been enlarged with the addition of a medium within the reservoir such that the overall dimension of the body portion plus the expanded reservoir (356) may be greater than the inner dimension of a stricture point or narrowing. In said embodiment, the reservoir may create a flanged portion that can alter between one or more states. Through certain embodiments utilizing an expandable reservoir, the embodied device or prosthesis may be fixated within the stricture point or narrowing, as illustrated in FIG. 2C. The embodied device or prosthesis may be seated on a stricture point or narrowing (357) where the flanged portion (351) may present a force that may be preventing the intragastrointestinal device from moving in the direction of the proximal portion of the gastrointestinal tract (359) into the distal portion of the gastrointestinal tract (358). The expandable reservoir in an expanded state (356) may present a force that may prevent or resist the embodied device or prosthesis from moving in the direction of the distal portion of the gastrointestinal tract (358) into the proximal portion of the gastrointestinal tract (359). In such embodiments, the embodied device or prosthesis may be fixated or seated at a stricture point or narrowing.

Embodiments of the invention similar, but not exclusive of the embodiments illustrated in FIG. 2 may be used at stricture points or narrowings that may be created by means other than by a band of material wrapped around the stomach. Such stricture points or narrowings may be created by, but are not limited to, anastomoses or openings between the gastric lumen and the intestinal lumen, or between the gastric lumen and the esophageal lumen, or between the esophageal lumen and the intestinal lumen, or between the gastric lumen and at least a portion of the abdominal cavity, or between the intestinal lumen and at least a portion of the abdominal cavity, or between the esophageal lumen and at least a portion of the abdominal cavity. Embodiments of the present invention may be used at the junction between two lumens or cavities, including but not limited to between the esophageal lumen and the stomach lumen at or near the esophageal sphincter or between the stomach lumen and the intestinal lumen at or near the pyloric sphincter.

Further embodiments of the present invention may include an embodied intragastrointestinal device or prosthesis, where a flanged portion may be embodied by an expandable reservoir. In these embodiments, the expandable reservoir may be altered to an expanded state and the greatest dimension of the embodied device or prosthesis may be larger than the inner dimension of a stricture point or narrowing, allowing the embodied device or prosthesis to be fixated or seated at a stricture point or narrowing. Additionally, in certain embodiments, a second expandable reservoir, similar as but not limited to the embodiments shown in FIG. 2, may be incorporated. In certain embodiments of the invention, the embodied intragastrointestinal device or prosthesis may incorporate two or more expandable reservoirs, wherein one expandable reservoir may be incorporated into the distal portion of the embodied intragastrointestinal device or prosthesis, and one expandable reservoir may be incorporated into the proximal portion of the embodied intragastrointestinal device or prosthesis. When said embodiment is preferably seated at a stricture point and the two or more expandable reservoirs may be in their expanded state such that the greatest dimension of the body portion and the expandable reservoir may be greater than the internal dimensions of a stricture point, an expandable portion that resides within at least one portion of the gastrointestinal tract lumen may present an opposing force to the embodied device or prosthesis against moving in the direction of said portion of the gastrointestinal tract lumen to the portion of the gastrointestinal tract lumen on the other side of the stricture point. Such embodiments of the present invention may optionally have a distal portion incorporated into the embodied intragastrointestinal device or prosthesis which may act as a malabsorptive device element.

Figure 3:
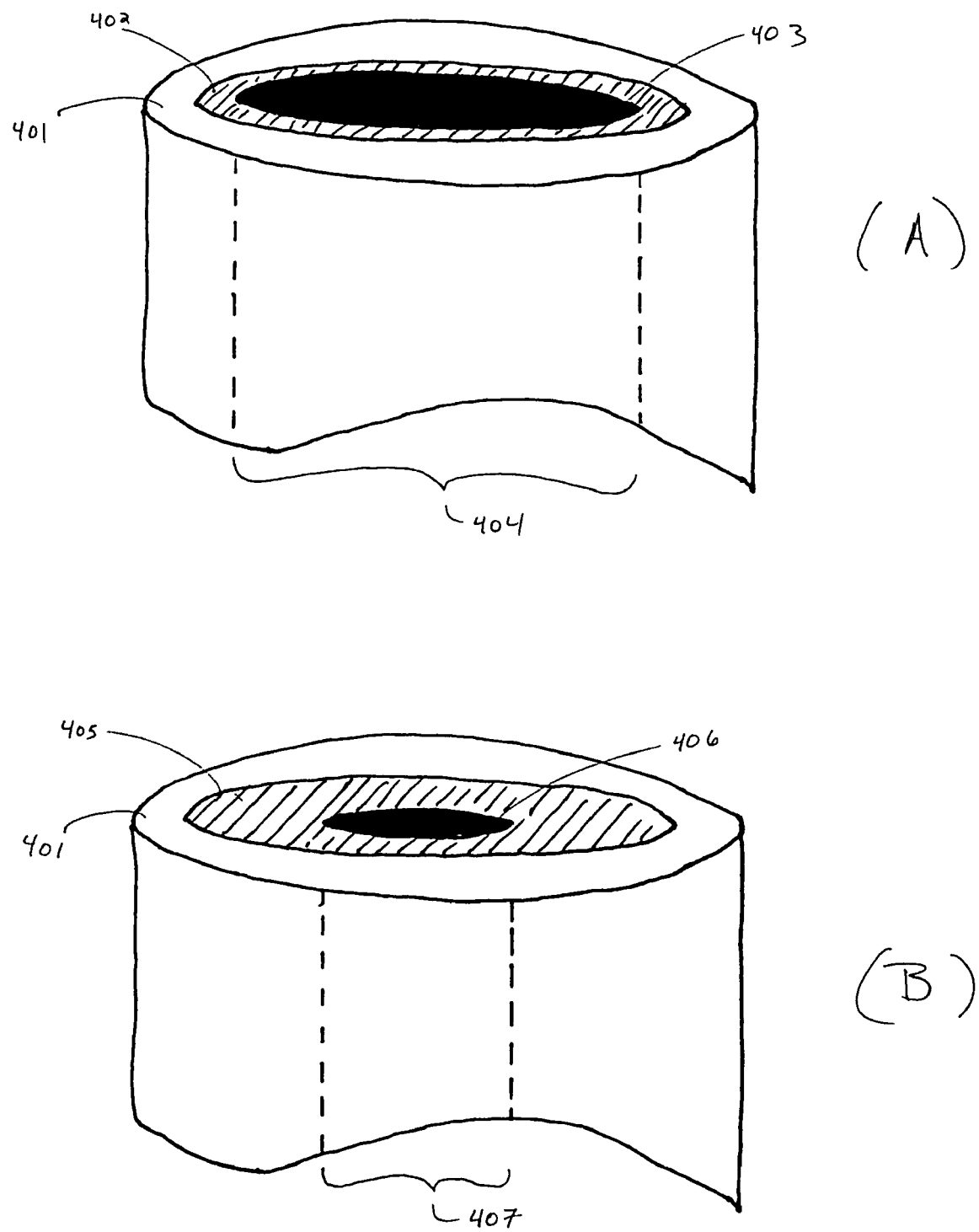
FIGS. 3A-3B illustrate an embodiment of an intragastrointestinal device or prosthesis with an adjustable lumen dimension.

In many embodiments of the invention, a restrictive device element may be incorporated. The restrictive device element may be implemented in some embodiments by creating a lumen within an embodied intragastrointestinal device or prosthesis such that it may impede or slow at least a portion of the flow of swallowed food and/or fluid. In preferred embodiments of the invention, the lumen or stoma size incorporated in the embodied device or prosthesis may be adjustable. As such, certain embodiments may have the ability to change the inner dimensions of the embodied device or prosthesis lumen. Said change in inner dimension may be based on the specific needs of the stomach, the gastrointestinal tract, or of the human. This aspect may be embodied and illustrated in FIG. 3. FIG. 3A demonstrates an embodiment which incorporates a larger internal dimension (403 & 404) of a lumen and/or lumen opening. In said embodiments, the body portion (401) may contain an adjustable portion (402) that can expand or contract. The expansion or contraction of the adjustable portion may change the dimensions of the lumen (404) or the entry into the lumen (403). FIG. 3B illustrates an embodiment where the adjustable portion (405) has a larger dimension, which may result in the lumen (407) or the entrance to the lumen (406) having a smaller dimension. By changing the lumen size or the size of the entry to the lumen, in certain embodiments at least a portion of the flow of swallowed food and/or fluid may be altered. It should be noted that certain embodiments may consist of an adjustable portion that changes the dimension of: the entrance to the lumen only, the lumen only, both the entrance to the lumen and the lumen, or other configurations.

Figure 4:
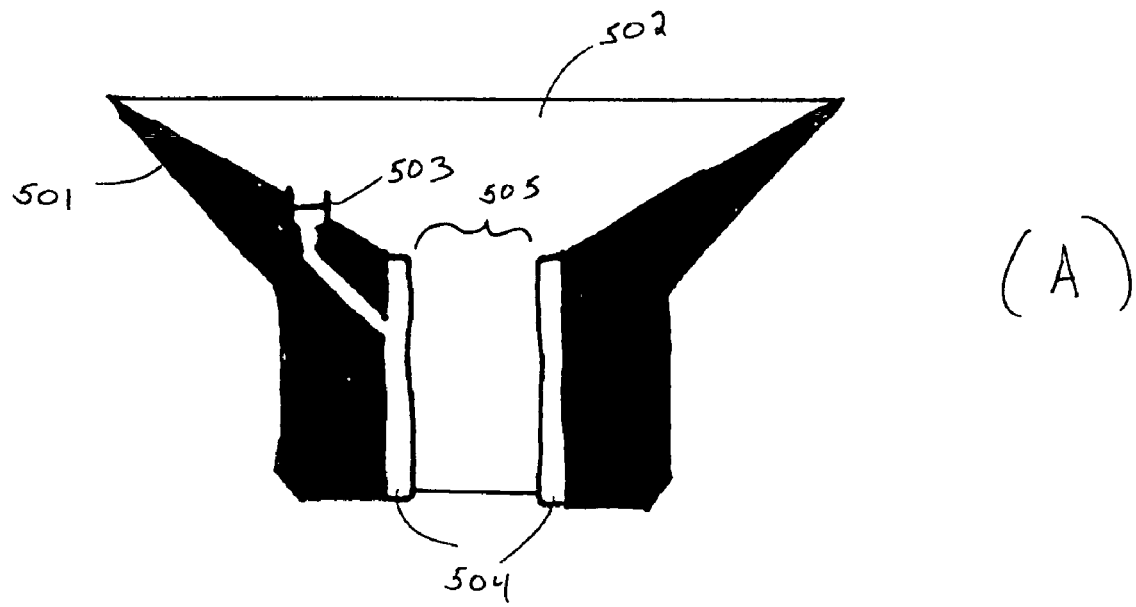
FIGS. 4A-4B illustrate an embodiment of an intragastrointestinal device or prosthesis with an adjustable lumen dimension at least partially regulated by an internal reservoir.
Figure 4:
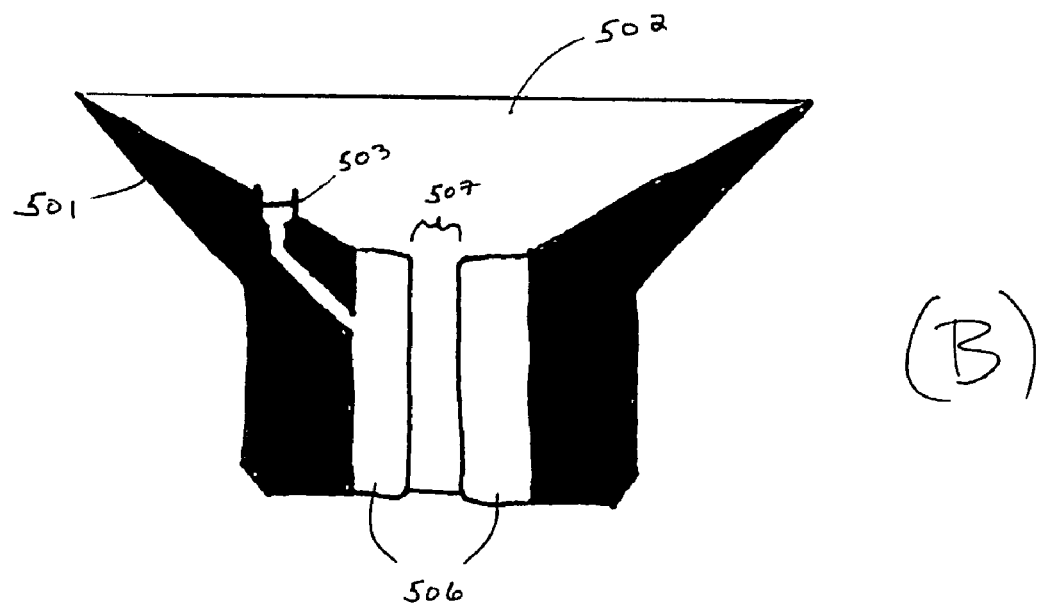

FIG. 4 illustrates a cross sectional view of a preferred embodiment of an intragastrointestinal device or prosthesis incorporating an adjustable lumen. In such an embodied device or prosthesis, similar to but not exclusive of the embodiment shown in FIG. 1, the embodiment may consist of a flanged portion (501 & 502) that may reside in the proximal portion of the stomach or gastrointestinal lumen. Food and/or fluid that are swallowed may enter the intragastrointestinal device from the opening in the flanged portion (502) into the lumen (505). The embodied device or prosthesis may incorporate an expandable reservoir (504 & 506) that may be incorporated as part of the body portion. Said reservoir may be filled with, but is not limited to, saline, fluid, or gas. The embodied intragastrointestinal device or prosthesis may also incorporate a reservoir port (503) that may be positioned on some portion of the embodiment (in FIG. 4, the port system is embodied on the flanged portion 501, although many other embodiments are possible). One embodiment of the port system that may be implemented on the embodied device or prosthesis may be a membrane which can be accessed by a needle or syringe. The embodiment may be designed such that the needle or syringe may increase or decrease the amount of medium within the reservoir. Said needle or syringe may be, but is not limited to, percutaneously or endoscopically delivered.

Other embodiments of the port system are also possible that allow the increase or decrease in the volume of medium within the expandable reservoir. One such embodiment of a port system can be implemented where a membrane portion of the port system is placed outside the gastric or gastrointestinal lumen. In said embodiments, the membrane portion would be connected to the embodied intragastrointestinal device or prosthesis through a tube or other connection portion which may be transgastric in nature. One example of such an embodiment would include the placement of the membrane portion within a subcutaneous pocket under the skin with a connection portion running through the stomach and/or gastrointestinal wall and attaching to the embodied device or prosthesis. In said example embodiment, the membrane portion may be accessed by percutaneous injection or removal with the use of a needle or syringe through the skin.

The reservoir port (503) may allow the embodied intragastrointestinal device or prosthesis to expand or contract the expandable reservoir (504 & 506). FIG. 4A demonstrates an expandable reservoir (504) in one state where the dimension of the lumen (505) may be large. FIG. 4B demonstrates an expandable reservoir (506) in a state where the dimension (507) of the lumen may be small. By adjusting the dimension of the lumen to a preferred dimension, a preferred rate of flow or a portion of rate of flow for swallowed food and/or fluid may be obtained. In certain embodiments of the present invention, the use of an expandable reservoir may create a restrictive device element within the embodied device or prosthesis.

Certain embodiments of the invention may include a combination of embodied aspects in FIG. 1, FIG. 2, FIG. 3, and/or FIG. 4. This may include, but is not limited to, the use of an expandable reservoir or other means that may aid in fixation and a second expandable reservoir or other means that may adjust the lumen of the embodied device or prosthesis. Other embodiments may include the use of an expandable reservoir or other means that may fill the space between the stricture point or narrowing and the body portion of the embodied device or prosthesis. In such embodiments, the expandable reservoir or other means may create an engagement between the embodied device and the stricture point, such that the engagement be, but not be limited to, water-tight, air-tight, and/or particle-tight. Certain embodiments may incorporate an expandable reservoir or other means, wherein the expandable reservoir or other means may act as a restrictive device element.

Certain embodiments of the present invention may be implanted or deployed by means including, but not limited to, an open surgical procedure, a laparoscopic surgical procedure, a minimally invasive surgical procedure, a flexible or partially flexible endoscopic procedure. Certain embodiments of the present invention may be at least part of one or more medical procedures that may include, but are not limited to, a bariatric procedure, a gastrointestinal procedure, a general surgery procedure, and a procedure related to gastric reflux disease.

Certain embodiments of the invention may incorporate an adjustable lumen. Such embodiments may adjust the lumen size such that the lumen is nearly or completely closed. By closing the lumen of the embodied device, the device may regulate or prevent the flow of intragastrointestinal content, including but not limited to, swallowed food and/or fluid, from passing trough the device. If the embodied device is seated at a stricture point and the engagement between the device and the stricture point is possibly air-tight and/or fluid-tight, the embodied device may regulate or prevent the flow of intragastrointestinal content, including but not limited to, swallowed food and/or fluid, through the stricture point. This embodiments may allow the device to close off or partially closed off a junction, anastomosis, or passageway between one or more lumens or cavities.

It is, of course, understood that modification of the present invention, in its various aspects, will be apparent to those skilled in the art. Additional method and device embodiments are possible, their specific features depending upon the particular application. For example, multiple expandable reservoirs may be used to aid fixation and be incorporated into restrictive device elements. Additionally, certain embodiment may be applicable to other portions of the gastrointestinal tract not named herein. Further, certain embodiments may be applicable to other organ systems in addition to the gastrointestinal tract.

What is claimed is:

1. An intragastrointestinal device comprising:
a body portion that is configured to be placed within at least a portion of a gastrointestinal tract lumen, the body portion having at least one device lumen extending therethrough that provides a restrictive element to restrict passage of food and/or fluid through the body portion, at least one dimension of the device lumen being manually adjustable by a user to any one of a plurality of different dimensions to vary a rate of flow through the device lumen; and
at least one fixation element located at a first end of the body portion, the fixation element being manually adjustable by the user to a plurality of states having different dimensions to aid in the fixation of the body portion in the gastrointestinal tract lumen, the fixation element being adjustable separate from the device lumen.

2. An intragastrointestinal device as in claim 1, wherein at least a portion of the body portion is configured to be positioned in proximity to a stricture point.

3. An intragastrointestinal device as in claim 2, wherein the stricture point is selected from a group comprising: a naturally occurring narrowing of a gastrointestinal tract lumen, a narrowing formed by at least a portion of a band of material wrapped around at least a portion of the gastrointestinal tract, an anastomosis between at least two lumens or cavities, a surgical opening between at least two lumens or cavities, and a constriction or restriction of at least a portion of a gastrointestinal tract lumen caused by at least a portion of a pathology.

4. An intragastrointestinal device as in claim 2, further comprising at least one flanged portion located at a second end of the body portion that is adapted to at least aid in the fixation of the device in proximity to the stricture point.

5. An intragastrointestinal device as in claim 2, wherein the at least one device lumen is adjustable such that no intragastrointestinal content, including swallowed food and/or fluid, can pass through the stricture point.

6. An intragastrointestinal device as in claim 1, wherein the at least one dimension of the device lumen comprises a diameter of the device lumen.

7. An intragastrointestinal device as in claim 1, further comprising at least one expandable reservoir that is manually adjustable to a plurality of different states to adjust the dimension of the device lumen.

8. An intragastrointestinal device as in claim 7, further comprising a reservoir port that at least partially allows the adjustment of the device lumen dimension, wherein the reservoir port is configured and arranged to be located at least one location selected from a group comprising: a location partially within the gastrointestinal lumen, and a location partially outside the gastrointestinal lumen.

9. An intragastrointestinal device as in claim 8, wherein the expandable reservoir contains at least one medium selected from a group comprising: a fluid, and a gas.

10. An intragastrointestinal device as in claim 9, wherein the reservoir port comprises a membrane, and wherein the medium can be added to or removed from the reservoir through the membrane either endoscopically, percutaneously, or a combination of the two.

11. An intragastrointestinal device as in claim 8, wherein the reservoir port is configured and arranged to be located at least partially outside the gastrointestinal lumen and the adjustment of the at least one device lumen dimension is accomplished percutaneously through the skin with a syringe or needle.

12. An intragastrointestinal device as in claim 1, wherein the device lumen is adjustable to provide a specified rate of flow of food and/or fluid through the gastrointestinal tract lumen.

13. An intragastrointestinal device as in claim 1, wherein the device is configured to be deployed by at least a method selected from a group comprising: an open surgical procedure, a laparoscopic surgical procedure, and an at least partially flexible endoscopic procedure.

14. An intragastrointestinal device as in claim 1, wherein the device is configured to be used as at least a portion of a medical procedure selected from a group comprising: a bariatric procedure, a gastrointestinal procedure, a general surgery procedure, and a procedure related to gastric reflux disease.

15. An intragastrointestinal device as in claim 1, further comprising at least one distal portion that is coupled to the body portion and is configured to at least partially act as a malabsorptive device element.

16. An intragastrointestinal device comprising:
a body portion that is configured to be placed within at least a portion of a gastrointestinal tract lumen, the body portion having a device lumen to allow passage of food and/or fluid therethrough, at least a portion of the body portion having an outer surface that defines an outer width thereof and is configured to extend through a stricture point, at least one dimension of the device lumen being manually adjustable by a user to any one of a plurality of different dimensions to vary a rate of flow through the device lumen; and
at least one adjustable portion located at a first end of the body portion and configured to be positioned only on a first side of the stricture point, the adjustable portion being manually adjustable by a user to a plurality of states with different dimensions to vary the size of the first end, at least one of the states setting the size of the first end to be greater than the outer width of the portion of the body portion to at least aid in the fixation of the intragastrointestinal device in proximity to the stricture point.

17. An intragastrointestinal device as in claim 16, wherein the stricture point is selected from a group comprising: a naturally occurring narrowing of a gastrointestinal tract lumen, a narrowing formed by at least a portion of a band of material wrapped around at least a portion of the gastrointestinal tract, an anastomosis between at least two lumens or cavities, a surgical opening between at least two lumens or cavities, and a constriction or restriction of at least a portion of a gastrointestinal tract lumen caused by at least a portion of a pathology.

18. An intragastrointestinal device as in claim 16, wherein the at least one adjustable portion comprises a flanged portion.

19. An intragastrointestinal device as in claim 16, wherein the at least one adjustable portion is adjustable to at least one of the states selected from a group comprising: a state wherein the dimensions of the adjustable portion and the body portion together are greater than an inner dimension of the stricture point, and a state wherein the dimensions of the adjustable portion and the body portion together are less than an inner dimension of the stricture point.

20. An intragastrointestinal device as in claim 16, wherein the at least one adjustable portion comprises an expandable reservoir that is manually adjustable to a plurality of different states.

21. An intragastrointestinal device as in claim 16, further comprising a flanged portion located at a second end of the body portion, the flanged portion configured and arranged to be positioned on a second side of the stricture point, the flanged portion having a width that is greater than the outer width of the portion of the body portion to aid in the fixation of the intragastrointestinal device in proximity to the stricture point.

22. An intragastrointestinal device as in claim 16, further comprising at least one adjustable portion located at a second end of the body portion and configured to be positioned only on a second side of the stricture point, the adjustable portion being manually adjustable by a user to a plurality of states with different dimensions to vary the size of the second end, at least one of the states setting the size of the second end to be greater than the outer width of the portion of the body portion to at least aid in the fixation of the intragastrointestinal device in proximity to the stricture point.

* * * * *